United States Patent
Massaro

(10) Patent No.: US 7,125,727 B2
(45) Date of Patent: Oct. 24, 2006

(54) SAMPLE HANDLING TOOL WITH PIEZOELECTRIC ACTUATOR

(75) Inventor: Peter Massaro, Burlington, CT (US)

(73) Assignee: Protedyne Corporation, Windsor, CT (US)

( * ) Notice: Subject to any disclaimer, the term of this patent is extended or adjusted under 35 U.S.C. 154(b) by 532 days.

(21) Appl. No.: 10/353,317

(22) Filed: Jan. 29, 2003

(65) Prior Publication Data

US 2004/0146433 A1    Jul. 29, 2004

(51) Int. Cl.
*G01N 1/10*    (2006.01)
*B01L 3/02*    (2006.01)

(52) U.S. Cl. .................. 436/180; 422/100; 422/63; 73/863.32; 73/864; 73/864.01; 73/864.02; 73/864.13; 73/864.11

(58) Field of Classification Search .......... 422/50–100; 436/180
See application file for complete search history.

(56) References Cited

U.S. PATENT DOCUMENTS

| | | | |
|---|---|---|---|
| 4,298,575 A * | 11/1981 | Berglund ................. | 73/864.13 |
| 4,405,344 A | 9/1983 | Sisti et al. | |
| 4,481,713 A * | 11/1984 | Howell ...................... | 33/39.2 |
| 4,622,483 A | 11/1986 | Staufenberg, Jr. et al. | |
| 4,671,123 A | 6/1987 | Magnussen, Jr. et al. | |
| 4,715,413 A | 12/1987 | Backlund et al. | |
| 4,905,526 A | 3/1990 | Magnussen, Jr. et al. | |
| 5,053,100 A | 10/1991 | Hayes et al. | |
| 5,133,392 A | 7/1992 | Hamann | |
| 5,187,990 A | 2/1993 | Magnussen, Jr. et al. | |
| 5,333,495 A | 8/1994 | Yamaguchi et al. | |
| 5,567,122 A | 10/1996 | Schulte | |
| 5,763,278 A | 6/1998 | Sickinger et al. | |
| 5,877,580 A | 3/1999 | Swierkowski | |
| 5,882,317 A | 3/1999 | Saito et al. | |
| 5,957,167 A | 9/1999 | Feygin | |
| 5,958,343 A | 9/1999 | Astle | |
| 5,964,381 A | 10/1999 | El-Hage et al. | |
| 5,969,465 A | 10/1999 | Neukermans et al. | |
| 6,062,212 A | 5/2000 | Davison et al. | |
| 6,232,129 B1 | 5/2001 | Wiktor | |
| 6,245,297 B1 | 6/2001 | Kowallis | |
| 6,280,148 B1 | 8/2001 | Zengeric et al. | |
| 6,296,702 B1 | 10/2001 | Bryning et al. | |
| 6,355,487 B1 | 3/2002 | Kowallis | |
| 6,372,185 B1 | 4/2002 | Shumate et al. | |
| 6,387,330 B1 | 5/2002 | Bova et al. | |
| 6,398,281 B1 | 6/2002 | Heimberg | |
| 6,403,338 B1 | 6/2002 | Knapp et al. | |
| 6,407,437 B1 | 6/2002 | Burger et al. | |
| 6,408,884 B1 | 6/2002 | Kamholz et al. | |
| 6,411,433 B1 | 6/2002 | Miyoshi | |
| 6,413,586 B1 | 7/2002 | Vann et al. | |
| 6,415,821 B1 | 7/2002 | Kamholz et al. | |

(Continued)

FOREIGN PATENT DOCUMENTS

CH    627552    1/1982

(Continued)

OTHER PUBLICATIONS www.edoceramic.com Copyright 2002.*

(Continued)

*Primary Examiner*—Brian R. Gordon
(74) *Attorney, Agent, or Firm*—Wolf, Greenfield & Sacks, P.C.

(57) ABSTRACT

A material handling tool includes a piezoelectric motor that causes actuation of a needle. Actuation of the needle may include aspiration and/or dispensing of a fluid sample and/or movement of the needle to pick or place a material sample.

27 Claims, 5 Drawing Sheets

U.S. PATENT DOCUMENTS

| | | | |
|---|---|---|---|
| 6,416,294 B1 | 7/2002 | Zengeric et al. | |
| 6,429,016 B1 | 8/2002 | McNeil | |
| 6,431,015 B1 | 8/2002 | Hodac et al. | |
| 6,440,217 B1 | 8/2002 | Vann et al. | |
| 6,440,370 B1 | 8/2002 | Blum et al. | |
| 6,440,722 B1 | 8/2002 | Knapp et al. | |
| 6,444,461 B1 | 9/2002 | Knapp et al. | |
| 6,558,127 B1 * | 5/2003 | Maruyama et al. | 417/44.1 |
| 6,592,825 B1 * | 7/2003 | Pelc et al. | 422/100 |
| 6,617,766 B1 * | 9/2003 | Stoecklein et al. | 310/346 |
| 6,656,432 B1 * | 12/2003 | Hirota et al. | 422/100 |
| 6,679,685 B1 * | 1/2004 | Maruyama et al. | 417/374 |
| 6,860,148 B1 * | 3/2005 | Kossuth et al. | 73/159 |
| 6,869,571 B1 * | 3/2005 | Ingenhoven et al. | 422/100 |
| 6,890,485 B1 * | 5/2005 | Stylli et al. | 422/68.1 |
| 2001/0016358 A1 | 8/2001 | Osawa et al. | |
| 2001/0036424 A1 * | 11/2001 | Takahashi et al. | 422/100 |
| 2002/0009394 A1 | 1/2002 | Koster et al. | |
| 2002/0017464 A1 | 2/2002 | Parce et al. | |
| 2002/0045272 A1 | 4/2002 | McDevitt et al. | |
| 2002/0051737 A1 | 5/2002 | Sollböhmer et al. | |
| 2002/0072096 A1 | 6/2002 | O'Keefe et al. | |
| 2002/0095998 A1 | 7/2002 | Kriz et al. | |
| 2002/0106308 A1 * | 8/2002 | Zweifel et al. | 422/100 |
| 2002/0119077 A1 | 8/2002 | Shumate et al. | |
| 2002/0131903 A1 * | 9/2002 | Ingenhoven et al. | 422/100 |
| 2002/0159919 A1 | 10/2002 | Churchill et al. | |
| 2004/0219688 A1 * | 11/2004 | Churchill et al. | 436/180 |
| 2005/0232094 A1 * | 10/2005 | Hoshino | 369/44.11 |

FOREIGN PATENT DOCUMENTS

| | | |
|---|---|---|
| EP | 0428500 A2 | 5/1991 |
| EP | 1103305 A1 | 1/1998 |
| EP | 0865824 A1 | 9/1998 |
| EP | 0815940 A3 | 5/2001 |
| EP | 1101532 A2 | 5/2001 |
| GB | 1453978 | 10/1976 |

OTHER PUBLICATIONS

ISA Written Opinion, International Application No.: PCT/US2004/002499, mailing date Aug. 11, 2005.

* cited by examiner

SAMPLE HANDLING TOOL WITH PIEZOELECTRIC ACTUATOR

BACKGROUND OF INVENTION

1. Field of Invention

This invention relates to sample handling tools, such as robotically-manipulated pipetting devices.

2. Related Art

Robotically manipulated tools having a plurality of pipette channels are widely used, for example, in proteomic and genomic research. These devices are used to move material samples both to and from a variety of different work areas, such as microtiter trays, gels having separated DNA fragments, and other material holding apparatus. Some such tools may have a plurality of needles, e.g., having attached pipette tips, arranged in an array that corresponds to wells in a microtiter tray, such as the commonly-known 96-well or 384-well plate. The array of needles, when arranged to correspond with all of the wells in a microtiter tray, may allow material samples to be simultaneously deposited in, and removed from, wells in the microtiter tray, thus increasing the speed at which the samples in the microtiter tray may be processed.

SUMMARY OF INVENTION

Aspects of the invention provide a sample handling tool that uses a piezoelectric motor to cause needles to pick up and/or place a sample on a work surface. In one illustrative embodiment, a piezoelectric motor may be used to drive a plunger in a cavity. Movement of the plunger in the cavity can cause fluid to be aspirated and/or dispensed at a needle and/or cause movement of the needle associated with the cavity. As used herein, piezoelectric motor refers to a device that uses piezoelectric elements to move a drive element within a range of at least ⅛ inch or more. This is in contrast to a range of movement of a single piezoelectric element that is not itself capable of moving distances of ⅛ inch or more. In one embodiment, the piezoelectric motor may be capable of moving a drive element in a range of distances, such as 0.125 inches, 0.25 inches, 1.0 inch, 2.0 inches, or more, with an accuracy of down to approximately 1 micron.

In one aspect of the invention, a sample handling device includes a body having at least one cavity formed therein, and a needle in fluid communication with the cavity. A piezoelectric motor is adapted to move a drive element a distance of at least ⅛ inch such that movement of the drive element causes actuation of the needle in connection with the handling of a material sample.

In one aspect of the invention, a sample handling device includes a body having at least one elongated cavity formed therein, and a needle in fluid communication with a first end of the cavity. A plunger is moveable axially in the elongated cavity, and a piezoelectric motor moves the plunger axially in the elongated cavity to actuate the needle to handle a material sample with respect to a work surface.

In one aspect of the invention, a method for handing material samples includes providing a movable element positioned at least in part within a cavity that is in fluid communication with a needle adapted to handle a material sample. The movable element is moved a distance of at least ⅛ inch via a piezoelectric motor, and a material sample is moved via the needle based on movement of the movable element.

BRIEF DESCRIPTION OF DRAWINGS

The accompanying drawings, are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Various aspects of the invention are described below with reference to illustrative embodiments. However, it should be understood that the invention is not limited to those embodiments described below, but instead may be used in any suitable system or arrangement.

In one aspect of the invention, movement of a drive shaft in a piezoelectric motor may cause movement of an element in a pipettor that causes an associated needle to pick up and/or place a material sample. As used herein, a pipettor is a device that includes at least one needle, e.g., a hollow tube section, and associated devices that cause actuation of the needle. As used herein, actuation of a needle refers to causing the needle to operate in a way such that it can handle a material sample, i.e., aspirate and/or dispense a fluid sample and/or cause the needle to move, such as when picking up a sample from a gel or placing the sample on another work surface. (As used herein, fluid refers to both gases and/or liquids.) For example, the pipettor may include one or more cavities within which a plunger or other movable element may move. Movement of the plunger or other moveable element may cause a pressure change in the cavity, thereby causing a fluid or other material sample to be aspirated or dispensed in an associated needle. Accordingly, movement of the movable element in the cavity actuates the associated needle.

In one aspect of the invention, movement of a plunger or other movable element in a pipettor may be caused by a piezoelectric motor. Thus, a single piezoelectric motor may be used to control the actuation of a single needle, or may be used to control the actuation of a plurality of needles. A needle may be arranged to work with another element, such as a removable pipette tip, to handle material samples, or may handle material samples directly.

In one aspect of the invention, movement of sample handling needle may be controlled by a piezoelectric motor and a capacitive sensor that detects a position of the needle relative to a liquid. The capacitive sensor may provide information to a controller regarding the position of the needle relative to a liquid. Based on this information, the controller may instruct the piezoelectric motor to move the needle so it is positioned appropriately with respect to a top surface of the liquid.

Figure 1:
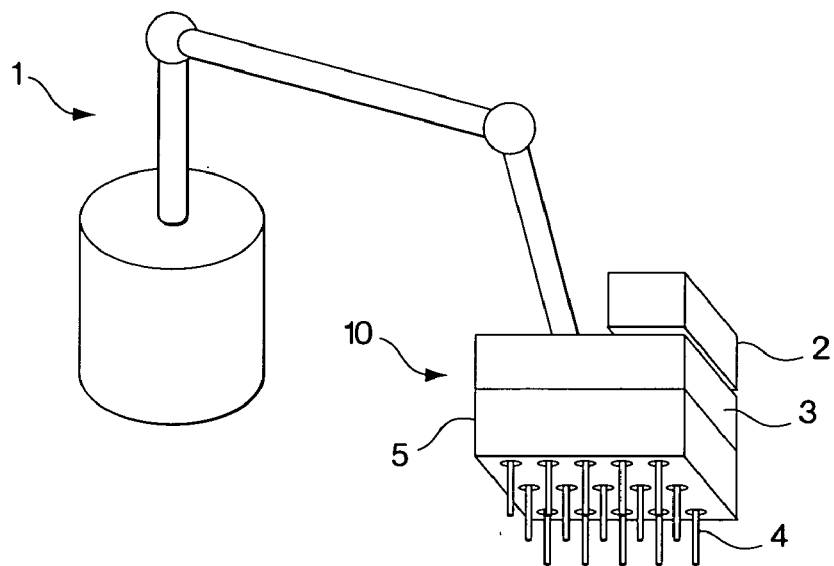
FIG. 1 is a schematic diagram of a robotically manipulated tool in accordance with the invention.

FIG. 1 is a schematic diagram of a robot 1 manipulating a material handling tool 10 in accordance with the invention.

The robot 1 may move the material handling tool 10 and allow needles 4 on the tool 10 to pick up and/or deposit material on one or more work areas, such as microtiter trays, gels containing separated DNA fragments or other biologic materials, etc. For example, the robot 1 may move the tool 10 so that one or more needles 4 are appropriately positioned with respect to a microtiter tray and then actuate one or more needles 4 to remove material from, or deposit material in, wells in the microtiter tray. Those of skill in the art will understand that the needles may be actuated to perform other material handling operations, such as colony or plaque picking at the direction of a machine vision system or other suitable control. The purposes and methods for such material handling are well known to those in the art and are not described in detail herein.

Although the robot 1 is shown in FIG. 1 as having a base and an articulated arm, the robot 1 may be of any suitable type or construction and may be capable of moving the tool 10 in any suitable number of degrees of freedom. For example, the robot may be a gantry-type robot capable of moving the tool 10 in three degrees of freedom. Of course, other suitable robotic configurations capable of moving the tool 10 in one or more degrees of freedom may be used. The tool 10 and robot 1 may include a coupling to allow the robot 1 to exchange the tool 10 for other tools, thereby allowing the robot 1 to perform automated operations with different tools. In addition, the connection between the tool 10 and the robot 1 may provide physical support to the tool 10 as well as provide electrical power, control signals, a fluid supply or other fluid signal, etc. The robot 1 or system controller may include a vision system or other suitable device to control positioning of needles 4 with respect to target areas, as is well known.

In the illustrative embodiment of FIG. 1, the tool 10 includes a controller 2 that outputs signals to one or more piezoelectric motors 3 that cause corresponding needles 4 to be actuated. As discussed above, actuation of a needle 4 may cause the needle 4 to move relative to the tool 10, such as extend away from the tool to pick or place material on a work area, control flow in the needle, such as drawing fluid into or expelling fluid out from the needle, or otherwise cause the needle to perform one or more material handling functions. In this illustrative embodiment, the controller 2, one or more motors 3 and needles 4 are all mounted to a body 5 of the tool 10. Although in this embodiment, the body 5 has a box-like shape, the body 5 may be arranged in any suitable way. Further, the needles 4 in this illustrative embodiment are arranged in a 4×4 array and extend from a bottom of the body 5, but any suitable number of needles 4 may be arranged in any suitable way on the body 5, e.g., to accommodate particular well patterns in a microtiter tray. The needles 4 may be arranged to receive removable pipette tips or other devices to handle materials, or may be arranged to handle materials directly.

The controller 2, which may in some embodiments be provided off of the tool 10 or have components both on and off the tool 10, may provide any suitable signal or combination of signals to the piezoelectric motors 3 to actuate the needles 4. For example, the controller 2 may provide electrical signals, magnetic signals, optical signals, fluid signals (e.g., changes in fluid pressure and/or flow), or combinations of such signals, such as providing both an electrical and a fluid signal to the piezoelectric motors 3. Of course, the piezoelectric motors 3 may operate in conjunction with other devices, such as electrically-controlled fluid valves, relays, or other suitable devices to actuate one or more needles. For example, a piezoelectric motor may be used to extend a needle away from the body 5 while another actuator component, such as a metering piston or fluid valve, controls flow through the needle. The controller 2 may include a capacitive sensing system or other arrangement to detect the position of needles 4 relative to a work area, such as a surface of a liquid in a microtiter tray. Such capacitive systems are well known in the art, and operate to determine the relative positions of a liquid or other work surface and a needle. Information provided by the capacitive sensing system may be used by the controller 2 to cause the robot 1 and/or the piezoelectric motors 3 to appropriately move one or more needles 4 to a specific location relative to a liquid or other work surface.

The controller 2 may operate autonomously to actuate the needles 4 or operate at the direction of a higher level controller that is part of a material handling system. For example, the controller 2 may receive a signal to activate a particular needle or group of needles at a particular time and/or position of the tool 10 and generate and output appropriate signals to cause the desired actuation. The controller 2 may receive the signals in any suitable way, such as by wired and/or wireless link, and in any suitable format and/or communications protocol. The controller 2 and/or higher level controller may include any suitable general purpose data processing system, which can be, or include, a suitably programmed, general purpose computer or network of general purpose computers, and other associated devices such as communication devices and/or other circuitry or components necessary to perform the desired input/output or other functions. The controllers can be implemented at least in part as single special purpose integrated circuits, e.g., ASICs, or an array of ASICs, each having a main or central processor section for overall, system-level control and separate sections dedicated to performing various different specific computations, functions and other processes under the control of the central processor section. The controllers can also be implemented using a plurality of separate dedicated programmable integrated or other electronic circuits or devices, e.g., hard wired electronic or logic circuits, such as discrete element circuits or programmable logic devices. The controllers also may include other devices, such as information display devices, user input devices, such as a keyboard, user pointing devices, a touch screen or other user interface, data storage devices, communication devices, or other electronic circuitry or components.

Figure 2:
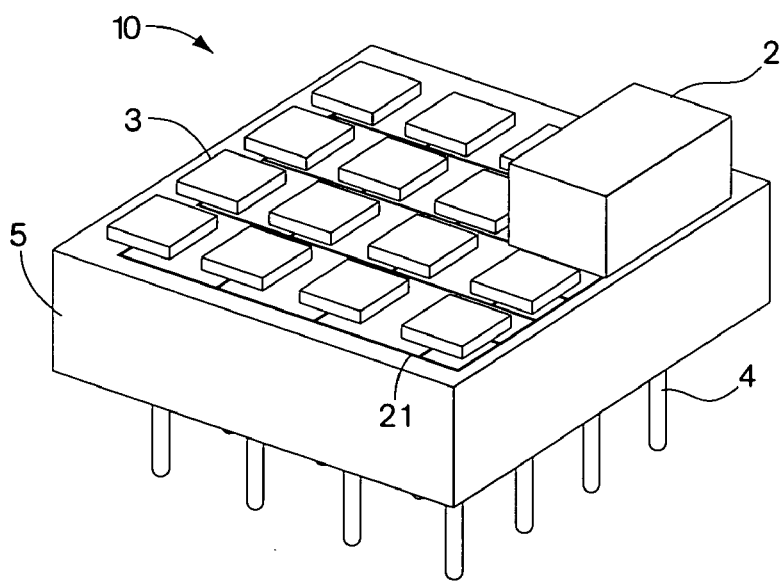
FIG. 2 is a schematic perspective view of a tool in accordance with the invention.
Figure 3:
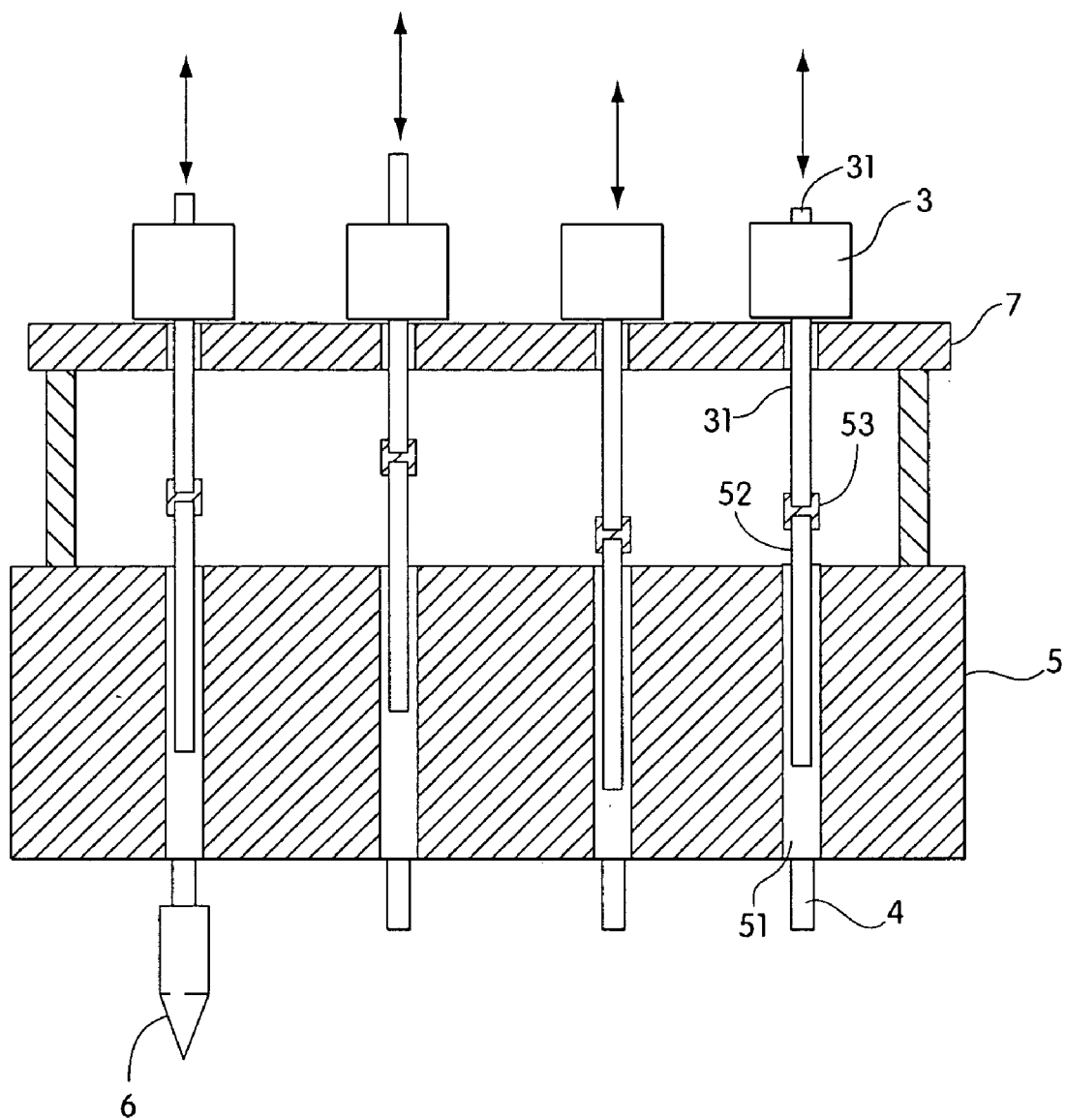
FIG. 3 is a cross-sectional view of a tool in one illustrative embodiment.

FIG. 2 shows a perspective view of a tool 10 in accordance with the invention. In this illustrative embodiment, the tool 10 includes a 4×4 array of piezoelectric motors 3 that are each associated with a corresponding needle 4. Thus, when a piezoelectric motor 3 receives appropriate signals, the corresponding needle 4 is actuated, e.g., fluid flow in the needle is controlled and/or the needle 4 is moved relative to the body 5. In this illustrative embodiment, the controller includes signal lines 21 to provide control signals to each of the piezoelectric motors 3. It should be understood that although the piezoelectric motors 3 in this illustrative embodiment are arranged in columns and rows, the motors 3 may be logically or physically grouped in any suitable way and in any suitable pattern. Further the tool 10 is not limited to a 4×4 array, but instead may have any suitable number of actuators and/or needles arranged in any suitable pattern, such as a standard 96-well, 384-well or other types of microtiter trays or other material sample holders. Thus, the 4×4 array in this illustrative embodiment is used for simplicity and ease of reference, but in no way should be interpreted as limiting aspects of the invention FIG. 3 shows a cross-sectional side view of a tool, such as that shown in FIG. 2, in accordance with the invention. In this illustrative embodiment, the tool body 5 includes a plurality of cavities 51, e.g., cylindrically shaped bores through the body 5. Each of these cavities 51 fluidly communicates with a corresponding needle 4. A moveable element, such as a plunger 52, may move within the cavity 51 and thereby control flow through the needle 4. For example, as a plunger 52 is withdrawn upwardly in a corresponding cavity 51, fluid may be drawn into the needle 4. The needle 4 may accept a pipette tip 6 or any other suitable device used for sample handling. The cavity 51 may be formed by boring or otherwise forming an opening in the body 5, or by providing an element, such as a cylinder liner, in the body 5. The plunger 52, like the body 5, may be made of any suitable material, such as glass, metal, plastic, etc. A seal may be formed between the plunger 52 and the cavity walls by a close fit, a lubricant, and/or a seal element, such as an elastomeric ring. Although in this embodiment, the cavities 51 are formed as cylindrical bores, the cavities 51 may have any suitable shape and/or size.

Movement of the plungers 52 in this illustrative embodiment is caused by a corresponding piezoelectric motor 3 mounted to a motor mount 7. A drive shaft 31 of the piezoelectric motor 3 is moved by the motor in up and down directions as shown in FIG. 3. This motion may be transmitted to the plunger 52 via a coupling 53. The coupling 53 may be formed in any suitable way, such as by an adhesive, an elastomeric part that engages the plunger 52 and drive shaft 31 by a friction fit, a threaded interconnection, etc. The coupling 53 may also allow for some minor misalignment between the drive shaft 31 and the plunger 52. Alternately, the coupling 53 need not be used and the drive shaft 31 may extend directly into the cavity 51 in place of the plunger 52.

Since in this illustrative embodiment each of the piezoelectric motors 3 is coupled to a corresponding pipette cavity, movement of the drive shaft 31 by the piezoelectric motor 3 actuates a corresponding needle 4. Thus, each needle 4 of the array on the tool 10 may be individually actuated by providing appropriate signals to the piezoelectric motors 3.

Figure 4:
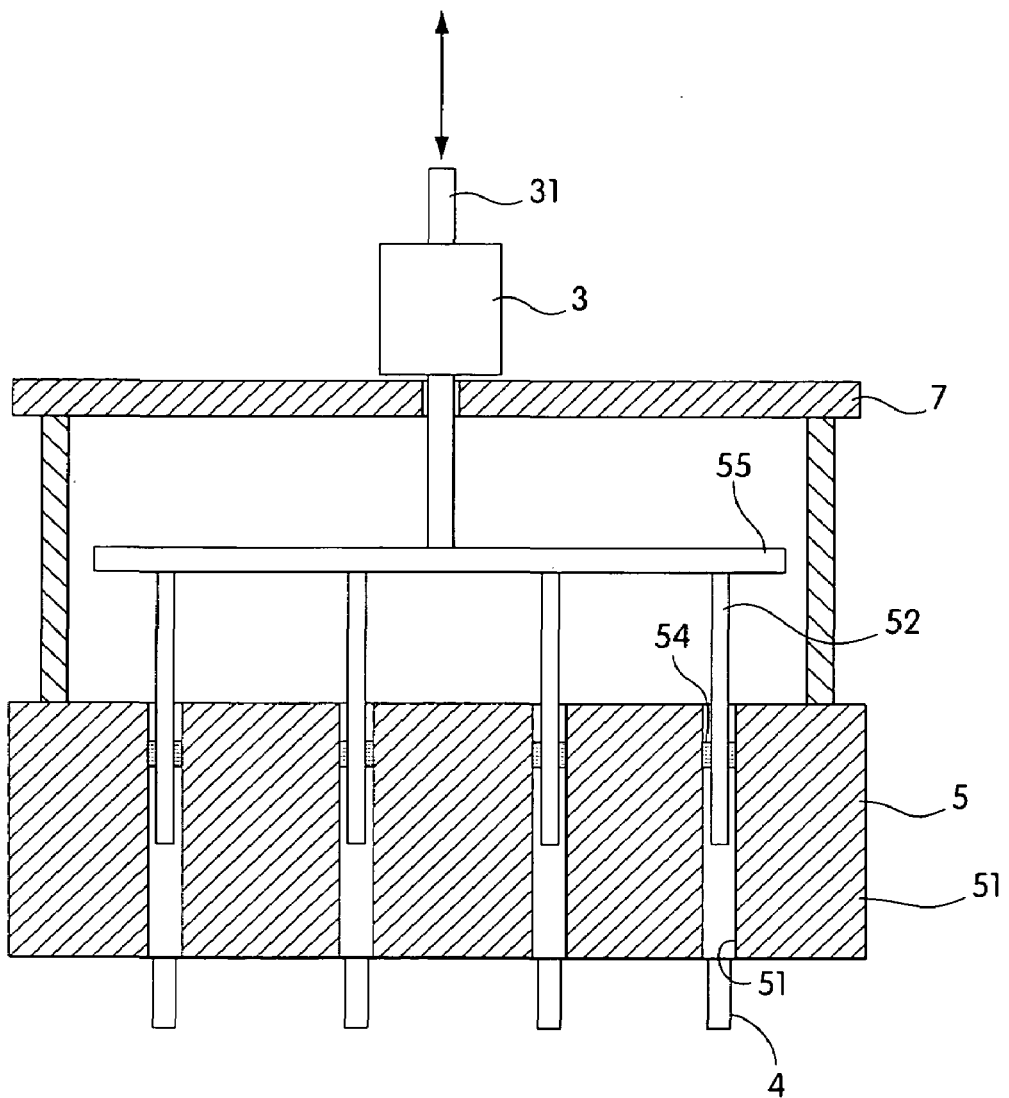
FIG. 4 is a cross-sectional view of a tool in another illustrative embodiment.

FIG. 4 shows a cross-sectional view of a tool 10 in accordance with another illustrative embodiment. This embodiment is similar to that shown in FIG. 3, except that a single piezoelectric motor 3 is used to control simultaneous, or approximately simultaneous, actuation of two or more needles, in this case at least four needles 4. That is, the drive shaft 31 of the piezoelectric motor 3 is linked to a drive bar or plate 55 coupled to one end of four or more plungers 52. Thus, as the piezoelectric motor 3 moves the drive bar 55 up and down, the plungers 52 linked to the drive bar 55 are controlled to move within a respective cavity 51. Movement of the drive bar or plate 55 may be guided by guideways, one or more rails, or other suitable structure to help make the plungers 52 move appropriately and consistently with respect to the body 5 and cavities 51. Position encoders or other sensors may also be used to determine the position, velocity and/or direction of movement of the drive bar or plate 55, drive shaft 31 and/or plunger 52, e.g., to provide feedback for control of the tool 10. Of course, it will be understood that the piezoelectric motor 3 may be linked in any suitable way to control any suitable number of needles 4. This illustrative embodiment also shows seals 54 that are used to create an air-tight or other suitable seal between the plungers 52 and the cavity 51 so flow in the needles 4 may be controlled.

Figure 5:
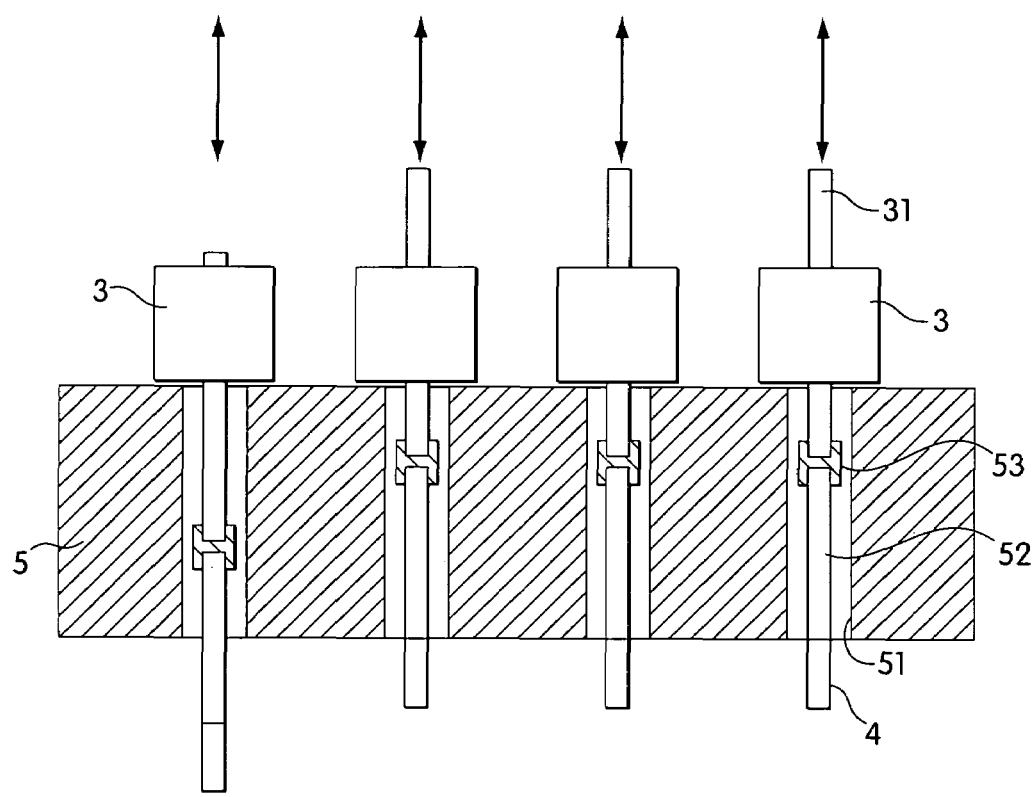
FIG. 5 is a cross-sectional view of a tool in yet another illustrative embodiment.

FIG. 5 shows a cross-sectional view of a tool 10 in accordance with yet another illustrative embodiment. Although in the FIGS. 3 and 4 embodiments actuation of the needles 4 includes controlling flow through a needle 4, the piezoelectric motors 3 may be arranged to move one or more corresponding needles 4 relative to the body 5, such as when extending a needle 4 away from the tool body to use the needle to individually pick a material sample from a work surface as shown in FIG. 5. In this illustrative embodiment, each piezoelectric motor 3 is coupled to a corresponding needle 4 (e.g., via a plunger 52) so that movement of the drive shaft 31 causes the needle 4 to move relative to the body 5. Such movement may allow the needle 4 to pick up and/or place a material sample. It will be understood that actuation of a needle may involve both movement of the needle and control of flow through the needle. One example of such operation may involve extending a needle away from the body 5 into a well in a microtiter plate, aspirating or dispensing fluid in the well, and retracting the needle. Those of skill in the art will also understand that a single piezoelectric motor may be used to both move a needle relative to the body 5 as well as control flow through the needle 4. Such control may be provided using an arrangement such as that shown in published U.S. Application No. US2001/0019845. Alternately, one piezoelectric motor 3 may be used to move the needle 4 relative to the body 5, and flow through the needle 4 may be controlled by other means, such as a metering piston, pump, or other mechanism fluidly coupled to the needle 4. A fluid coupling with the needle may be made, for example, via a channel through the center of the drive shaft 31 that communicates with a channel in the needle 4.

Figure 6:
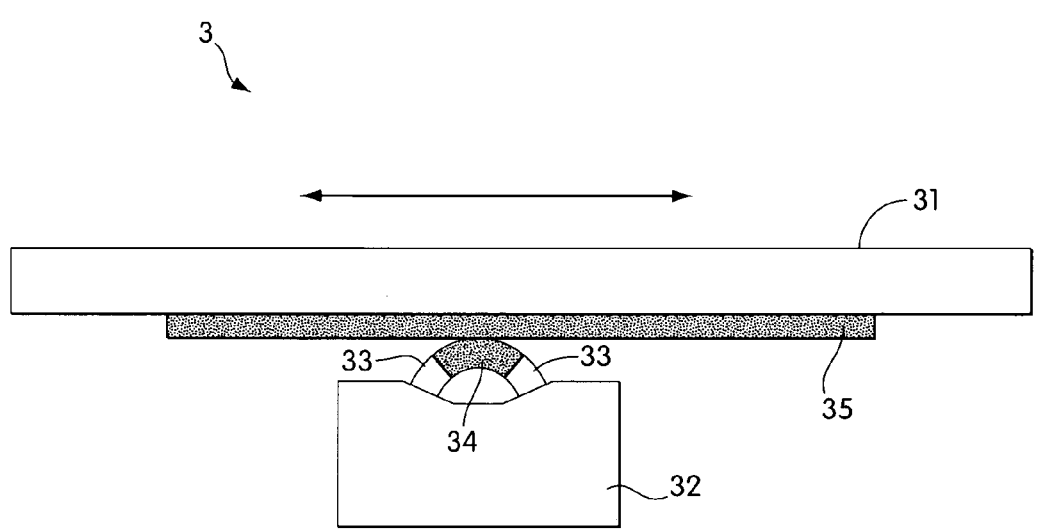
FIG. 6 is a schematic diagram of a piezoelectric motor in an illustrative embodiment.

Although the piezoelectric motor 3 may take any suitable form, FIG. 6 shows an illustrative embodiment of a piezoelectric motor 3 that may be used in accordance with the invention. In this illustrative embodiment, the piezoelectric motor 3 includes a housing 32 that supports a pair of piezoelectric elements 33 and a friction shoe 34. The friction shoe 34 engages with a friction strip 35 that is mounted to the drive shaft 31, e.g., by an adhesive. Appropriate electrical signals are provided to the piezoelectric elements 33 to vibrate the friction shoe 34 and cause it to engage with and move the friction strip 35 in a desired direction, i.e., to the left or right as shown in FIG. 6. One such piezoelectric motor is sold by EDO Electro-Ceramic Products of Salt Lake City, Utah under Model No. PDA130D. The piezoelectric motor 3 may be arranged to have multiple housings 32, and thus multiple friction shoes 34 that engage with one or more friction strips 35 on the drive shaft 31. By coupling multiple friction shoe/piezoelectric element combinations to a single drive shaft 31, the drive power supplied to the drive shaft 31 may be increased as desired. A piezoelectric motor as that shown in FIG. 6 may be capable of linear stroke lengths (a distance over which the drive shaft 31 may be moved) of 2–14 centimeters, although both shorter and longer stroke lengths are possible. The motor may drive the drive shaft 31 at speeds up to at least 20,000 centimeters per second at an accuracy of down to 1 micron. Any suitable position sensor may be used to detect the position and/or velocity of the drive shaft 31 and that information used to control movement of the drive shaft 31, as is well known in the art. For example, any suitable type of position encoder may be coupled to the drive shaft 31, the needle 4, or other movable part to provide information regarding the speed, distance of travel and/or position of the part. This information may be used to meter an amount of fluid that is aspirated and/or dispensed from a needle. Of course, other piezoelectric motor configurations than that shown in FIG. 6 may be used. However, in some embodiments, the piezoelectric motor should be arranged to provide a stroke length of at least ⅛ inch or larger to provide appropriate control of a corresponding needle.

This invention is not limited in its application to the details of construction and the arrangement of components set forth in the description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A sample handling device comprising:
   a body having at least one cavity formed therein;
   a needle in fluid communication with the cavity;
   a drive element; and
   a piezoelectric motor adapted to move the drive element over a stroke length of at least ⅛ inch, movement of the drive element causing actuation of the needle in connection with the handling of a material sample.

2. The device of claim 1, further comprising:
   a movable element disposed at least in part in the cavity and coupled to the drive element such that movement of the movable element in the cavity causes fluid flow in the needle.

3. The device of claim 1, further comprising:
   a plunger movably disposed in the cavity and coupled to the drive element, movement of the plunger causing fluid flow in the needle.

4. The device of claim 1, wherein the cavity includes a cylindrical bore, the device further comprising:
   a plunger having a cylindrical portion disposed in the cylindrical bore and coupled for movement with the drive element.

5. The device of claim 1, wherein the needle is adapted to receive a removable pipette tip.

6. The device of claim 1, further comprising:
   a coupling that mates with a corresponding coupling on a robotic manipulator such that the robotic manipulator may move and control the device to pick or place material samples.

7. The device of claim 1, comprising:
   a plurality of needles arranged in an array to cooperate with wells in a sample holder.

8. The device of claim 7, further comprising a plurality of piezoelectric motors, each of the plurality of piezoelectric motors associated with a corresponding needle, wherein each of the plurality of needles is individually actuatable to pick up or place a material sample and the actuation of each of the plurality of needles is controlled by a corresponding piezoelectric motor.

9. The device of claim 1, comprising:
   a plurality of needles that are simultaneously actuatable to handle material samples.

10. The device of claim 9, wherein actuation of the plurality of needles is controlled by one piezoelectric motor.

11. The device of claim 1, wherein the needle is movable relative to the body to handle a material sample.

12. The device of claim 1, wherein movement of the drive element causes fluid flow in the needle.

13. The device of claim 1, wherein the needle is actuatable by both being moved relative to the body and having flow controlled in the needle.

14. A sample handling device comprising:
    a body having at least one elongated cavity formed therein;
    a needle in fluid communication with a first end of the cavity;
    a plunger moveable axially in the elongated cavity; and
    a piezoelectric motor that is arranged to move the plunger axially in the elongated cavity over a stroke length of at least ⅛ inch to actuate the needle to handle a material sample with respect to a work surface, the piezoelectric motor being arranged to move the plunger to cause the needle to aspirate and dispense the material sample.

15. The device of claim 14, wherein the piezoelectric motor includes a drive element that is movable a distance of at least about ⅛ inch.

16. The device of claim 15, wherein the drive element is coupled to the plunger so that movement of the drive element causes axial movement of the plunger in the cavity.

17. The device of claim 14, wherein axial movement of the plunger causes movement of the needle relative to the body to actuate the needle.

18. The device of claim 14, wherein an approximately air tight seal is created between the plunger and the cavity so that movement of the plunger in the cavity causes fluid flow at the needle.

19. The device of claim 14, wherein the body has a plurality of elongated cavities, the device comprising a plurality of needles and a plurality of plungers each respectively corresponding to an associated cavity, the plurality of needles arranged to interact with a plurality of wells in a sample holder.

20. The device of claim 19, wherein the plurality of plungers are each associated with a corresponding piezoelectric motor so that movement of each of the plurality of plungers is individually controllable.

21. The device of claim 14, wherein the needle is adapted to receive a removable pipette tip.

22. The device of claim 14, further comprising:
    a coupling that mates with a corresponding coupling on a robotic manipulator such that the robotic manipulator may move and control the device to pick or place material samples.

23. A method for handing material samples, comprising:
    providing a movable element positioned at least in part within a cavity that is in fluid communication with a needle adapted to handle a material sample;
    moving the movable element over a stroke length of at least ⅛ inch via a piezoelectric motor; and
    moving a material sample via the needle based on movement of the movable element.

24. The method of claim 23, wherein the step of moving a material sample comprises:
    aspirating or dispensing a liquid sample at the needle.

25. The method of claim 23, wherein the step of moving the movable element comprises:
    moving a cylindrical plunger in a cavity to cause a pressure change at the needle in fluid communication with the cavity.

26. The method of claim 23, wherein the step of moving the movable element comprises:
using at least one piezoelectric element to incrementally move a drive element coupled to the movable element.

27. A sample handling device comprising:
a body having at least one cavity formed therein;
a needle in fluid communication with the cavity;
a drive element;
a piezoelectric motor adapted to move the drive element over a stroke length of at least 1/8 inch, movement of the drive element causing movement of the needle in connection with the handling of a material sample; and
a capacitive sensing system that provides information regarding a position of the needle relative to a work surface, the information used to control operation of the piezoelectric motor in moving the needle relative to the work surface.

* * * * *